United States Patent
Ella et al.

(10) Patent No.: US 8,956,812 B2
(45) Date of Patent: Feb. 17, 2015

(54) PROCESS FOR THE PREPARATION AND PURIFICATION OF RECOMBINANT PROTEINS

(75) Inventors: Krishna Murthy Ella, Hyderabad (IN); Srinivas Kannappa Vellimedu, Hyderabad (IN)

(73) Assignee: Bharat Biotech International Limited (IN)

( * ) Notice: Subject to any disclaimer, the term of this patent is extended or adjusted under 35 U.S.C. 154(b) by 423 days.

(21) Appl. No.: 10/585,030

(22) PCT Filed: Aug. 23, 2004

(86) PCT No.: PCT/IN2004/000257
§ 371 (c)(1),
(2), (4) Date: Jun. 29, 2006

(87) PCT Pub. No.: WO2005/063794
PCT Pub. Date: Jul. 14, 2005

(65) Prior Publication Data
US 2007/0154880 A1    Jul. 5, 2007

(30) Foreign Application Priority Data

Dec. 30, 2003 (IN) .......................... 1061/CHE/2003

(51) Int. Cl.
| | | |
|---|---|---|
| *C12Q 1/70* | (2006.01) | |
| *C12N 7/02* | (2006.01) | |
| *A61K 39/00* | (2006.01) | |
| *A61K 39/205* | (2006.01) | |
| *A61K 39/29* | (2006.01) | |
| *A61K 39/02* | (2006.01) | |
| *G01N 1/18* | (2006.01) | |
| *C07K 14/005* | (2006.01) | |
| *C07K 1/36* | (2006.01) | |

(52) U.S. Cl.
CPC ................. *C07K 14/005* (2013.01); *C07K 1/36* (2013.01); *C12N 2730/10122* (2013.01); *C12N 2760/20122* (2013.01); *C12N 2770/32422* (2013.01)

USPC ...... 435/5; 424/184.1; 424/224.1; 424/226.1; 424/227.1; 424/236.1; 435/239; 436/177

(58) Field of Classification Search
None
See application file for complete search history.

(56) References Cited

FOREIGN PATENT DOCUMENTS

WO    WO 03/050274    *    6/2003

OTHER PUBLICATIONS

Biology-Online dictionary, http://www.biology-online.org/dictionary/Vector, accessed on Aug. 29, 2008.*
Bitter et al., Hepatitis B Vaccine Produced in Yeast, 1988, Journal of Medical Virology, vol. 25, pp. 123-140.*
Lakshmi et al., Study of the safety, immunogenicity and seroconversion of a hepattiis-B vaccine in malnourished children in India, 2000, Vaccine, vol. 18, pp. 2009-2014.*
da Costa et al., Procedures for scaling up the recombinant 18kDa-hsp lepra protein production, 1995, Biotechnology Techniques, vol. 9, No. 7, pp. 527-532.*
Charnay et al., Biosynthesis of hepatitis B virVolus surface antigen in *Escherichia coli*, 1980, Nature, vol. 286, pp. 893-895.*
Brill et al., Recombinant tobacco mosaic virus movement protein is an RNA-binding, a-helical membrane protein, 2000, PNAS, vol. 97, No. 13, pp. 7112-7117.*
Manangeeswaran et al., Basic and Translational—Liver Binding of Hepatitis A Virus to Its Cellular Receptor 1 Inhibits T-Regulatory Cell Functions in Humans, 2012, Gastroenterology, vol. 142, pp. 1516-1525.*

\* cited by examiner

*Primary Examiner* — Benjamin P Blumel
(74) *Attorney, Agent, or Firm* — Roger Emerson; Emerson Thomson Bennett, LLC

(57) ABSTRACT

A novel process for the purification of recombinant protein expressed as particle is herewith described. In this purification process, the protein is purified by hydrophobic interaction. The interaction of this protein step resulted in an increase in recovery and purity from 15%-80%. The protein further purified has its application in vaccines and pharmaceuticals.

2 Claims, No Drawings

PROCESS FOR THE PREPARATION AND PURIFICATION OF RECOMBINANT PROTEINS

This application is the United States national stage of International Application No. PCT/IN2004/000257, filed Aug. 23, 2004, which was published under PCT Article 21 in English as International Publication No. WO 2005/063794, and which claims benefit of Indian Patent Application No. 1061/CHE/2003 filed Dec. 30, 2003.

The present invention further relates to a novel process for the preparation and purification of viral antigenic proteins and other recombinant therapeutic proteins produced in either prokaryotic or eukaryotic cell systems.

BACKGROUND OF INVENTION

Use of prokaryotic and eukaryotic cell systems for the production of various therapeutic protein molecules is a common method in present day Biotechnology. In this process, the protein of interest is expressed in the said cell system by suitably engineering the molecular genetics of the expression system to incorporate a plasmid to promote the production of the desired proteins when suitably induced during the growth of the cells.

Similarly, the use of various cell substrates for the multiplication of viruses for the production of viral antigens is also a common practice. In this process, the cells are multiplied to large volumes and then they are "infected" with the required virus to facilitate the growth of the viruses. Alternately, transfected cells can also be grown. The viral harvests are obtained from the culture supernates or by cell lysis.

In both the cases as above, the proteins of interest is then concentrated, purified and further treated suitably (inactivated or cleaved) to prepare a therapeutic preparation or vaccine as the case may be.

The major challenges in any of the above processes are the following.
a) Recovery of the protein or antigen of interest in a most economic way.
b) Purification of the protein of interest to eliminate the contaminating substances like the host cell proteins, media components and any other materials used in the process.
c) Concentration of the purified protein to enable further processing.
d) Maintenance of the functional structure and activity of the protein during various stages of purification and the efficiency of recovery.
e) Preparation of a product of therapeutic value at the end of the process which shows equal or better performance as that of the reference product.

In order to achieve the above objectives, various processes are adapted. Recombinant molecules can be expressed as heterologous proteins in yeasts such as *Sacharomyces cerevisiae*, *Pichia pastoris* or *E. coli* and other organisms. Many biopharmaceuticals and other polypeptides such as Hepatitis B, Insulin, Streptokinase, Erythropoeitin, Human Growth hormone have been produced by recombinant DNA technology. The expressed proteins are purified from the culture of expression host to obtain the product. Similarly several viral vaccines are also produced by culture in different types of primary or continuous cell lines. The virus grown thus is then suitably purified, concentrated and inactivated/or used as such for the preparation of vaccines.

Several steps of purification are generally adapted like clarification, centrifugation, filtration, and ultra-filtration, ammonium sulphate precipitation, use of silica beads, continuous centrifugation, rate zonal gradient centrifugation, various methods of chromatography like gel permeation, size exclusion, affinity and Ion-exchange, etc.

The purification processes named above have several drawbacks such as multiple steps, product loss, costly equipments and consumables and some times use of harmful chemicals like Cesium chloride, etc., and some of the processes make the product non-viable due to high cost of the 'down stream process'.

BRIEF DESCRIPTION OF THE INVENTION

According to the present invention as herein described, the recombinant proteins are made to be expressed in the vectors like *E. coli*, yeast, Eukaryotic cell, etc., extracted and purified by using HIMAX technology. It is understood that the word 'HIMAX' is coined by the inventors and refers to only the technology developed for this invention as explained hereunder.

OBJECTS OF THE INVENTION

1) The first object of the invention is to provide a method for the preparation and purification of recombinant proteins from the vectors by using HIMAX technology.
2) The second object of the invention is to prepare recombinant proteins which are highly purified without loss of biological activity.
3) The third object of the invention is to achieve negligible interference of the nucleic acid or other contaminants if any during the preparation of recombinant proteins.
4) The fourth object of the invention is to provide a process for simultaneous concentration and purification of various recombinant proteins, viral antigens and biotherapeutic molecules.
5) The fifth object of the invention is to provide a process of protein purification which is less time consuming and cost effective.
6) Another embodiment of the invention is to provide a process of purification of live and inactivated viral antigens from cell lysate and fluid.
7) The seventh object of the invention is to purify the recombinant proteins by using divalent cations like Zn, Ca, Mg, etc., in combination with anions like Acetate, Phosphate and chlorides.

Accordingly the present invention relates to a process for the preparation and purification of protein(s) such as viral antigenic proteins, other recombinant therapeutic proteins characterized in that the purification is carried out by a novel technique termed as HIMAX technology which is as herein described and recovering the said protein(s).

The present invention further relates to process and purification comprising:
(a) the vector cells are subjected to lysis in the absence of a detergent to obtain a cell lysate;
(b) subjecting the cell lysate of steps as to centrifugation ranging from 1000 g to 10,000 g;
(c) obtaining a solid from step (b) by decantation wherein the said solid comprising the said proteins;
(d) suspending the said solid in a buffer of pH 6 to 7.5 and optimally treating this with a detergent such as herein described to solubulize the minute impurities if any;
(e) as a part of HIMAX technology, the said protein(s) is/are captured by the addition of divalent ionic salt having concentration ranging from 0.2% to 10% with counter ions of either phosphate, chloride and/or acetate solution to form an insoluble matrix;

(f) subjecting the said insoluble matrix for centrifugation optimally to form pellets;

(g) subjecting repeated desorptions process to release the bound antigen from insoluble matrix/pellets by using either Tris buffer of Ph 8.0 to 8.5 or Tris buffer with EDTA at Ph 7.0 to 8.0;

(h) finally recovering the said proteins through ultrafiltration, chromatography on colloidal silica, hydrophobic and or affinity chromatography, ion exchange, diafiltration, sterile filtration or a combination thereof.

The present invention further relates to process and purification of toxoids such as Diphtheria and Tetanus

DETAILED DESCRIPTION OF THE INVENTION

Now the details of the present invention:
a) The desired protein obtained through recombinant expression method or by culture in suitable tissue culture is obtained in a clarified harvest after various steps like cell lysis, cell debris removal and clarification, etc.
b) A primary capture of the protein or antigen is carried out using the HIMAX method. Briefly the method involves using the addition of a divalent ionic salt ranging from 0.2% to 10% with counter ions of either phosphate, chlorides or acetate solution to form an insoluble matrix. The insoluble matrix thus obtained is then gently centrifuged to separate the bound antigen mass. The pellet thus obtained is then desorbed repeatedly with either Tris buffer of pH 8.0 to 8.5 or Tris buffer with EDTA at pH 7.0 to 8.0.
c) The desorbate containing the desired antigen is then further processed. In case of viral antigens, the process involved could be an inactivation followed by chromatography (ion exchange). In case of other antigens the desorbate is directly taken on to chromatography purification to obtain highly pure protein.
d) The final bulk product is obtained after pooling of the chromatographically purified fractions containing the desired proteins
followed by diafiltration and
e) or sterile filtration steps.

The above steps of invention are more clearly depicted in the following examples for some recombinant and cell culture proteins.

The examples provided herein are only for the explanation of the invention in detail and is not to be construed that the provided examples limits the scope of the present invention.

Varying options which are within the scope of the invention but are not covered in the description that are available to the persons skilled in the art are to be taken as included in the present invention.

Example-I

Hepatitis B Antigen Production from a Recombinant Pathway

The cell lysate after fermentation is subjected to centrifugation and the insoluble fraction is treated with detergent. The supernatant after centrifugation was either subjected to Aerosil adsorption and desorption (traditional technology) (table 1) or to primary capturing of HBsAg by a batch procedure in which salts of divalent cations such as Calcium, Magnesium and Zinc are added at 0.2% to 10% (w/v) in the presence of phosphates, Chlorides or Acetates to form white insoluble matrix. The insitu formation of the matrix further interact with the antigen and this process of protein capturing is referred as HIMAX technology (table 20). This matrix was separated by centrifugation between 7000 g to 10,000 g and bound antigen was desorbed repeatedly with this buffer of pH 8.5.

The desorbate was further purified using an anion exchange matrix namely the DEAE.

The HbsAg activity in all the intermediate steps is given in table I and table II.

In another strategy the cell lysate is directly subjected to primary capturing of the antigen by cations at 0.2 to 10% in the presence of phosphates, chlorides and acetates. All subsequent steps are similar to earlier procedure.

The HBs Ag activity in all the intermediate steps is given in table III.

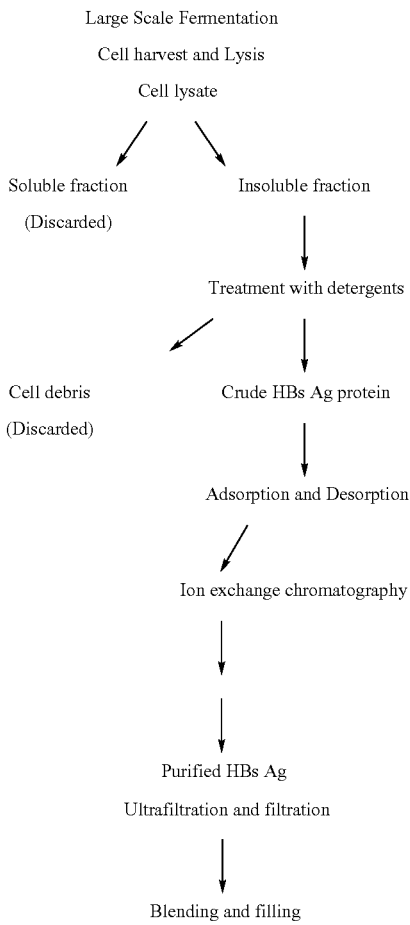

Flow Chart for HBs Ag production using HIMAX

TABLE I

Hepatitis B purification by traditional method

| S. No | Purification step | Activity (%) |
|---|---|---|
| 1. | Total cell Lysate | 100 |
| 2. | Soluble fraction | 9 |
| 3. | In soluble fraction (membrane bound) | 91 |
| 4. | Treatment with detergent | |
| 5. | Centrifugation | |
| 6. | Cell debris | 16 |

TABLE I-continued

| Hepatitis B purification by traditional method | | |
|---|---|---|
| S. No | Purification step | Activity (%) |
| 7. | Supernatent (HBsAg protein) | 34 |
| 8 | Binding to Aerosil and desorption | 20 |
| 9 | Ion exchange chromatography. | 15 |

TABLE II

| Hepatitis B purification by HIMAX method | | |
|---|---|---|
| .S. No | Purification step | Activity (%) |
| 1. | Cell Lysate | 100 |
| 2. | Soluble fraction | 9 |
| 3. | In soluble fraction (HBsAg membrane bound) | 91 |
| 4. | Treatment with detergent | |
| 5. | Centrifugation | |
| 6. | Supernatant (HBsAg protein) | 84 |
| 7. | Adsorption and desorption | 80 |
| 8 | Ion exchange chromatography. | 77 |

TABLE III

| Hepatitis B purification by HIMAX method | | |
|---|---|---|
| .S. No | Purification step | Activity (%) |
| 1. | Cell Lysate | 100 |
| 2. | Adsorption and Desorption | 90 |
| 3 | Ion Exchange chromatography | 80 |

The major difference between table 2 and table 3 is the usage of detergent,

In the table 2, the insoluble fraction is treated with detergent, and further processing Is carried with Adsorption and desorption technology.

While in the experiments represented in table 3, the cell lysate is directly subjected to adsorption and desorption by HIMAX technology.

Example II

Rabies Antigen Production from a Cell Culture Pathway

FIG. 2

The large scale virus culture facilitates obtaining Rabies virus in the culture supernates. Traditionally the harvests of virus thus obtained are concentrated by ultrafiltration and then purified using the gradient ultracentrifugation on sucrose in a continuous or batch mode zonal centrifuge. In the present invention the culture supernatants are initially purified by the use of HIMAX for primary capturing of rabies antigen by a batch procedure in which salts of divalent cations such as Calcium Magnesium and Zinc are added to yield a final concentration of 8 to 10 fold (W/V) resulting in the formation of white insoluble matrix further interacts. The insitu formation of the matrix further interact with the antigen and this process of protein capturing is referred as HIMAX technology. This matrix was separated by centrifugation between 7000 g to 10,000 g and the bound antigen was desorbed repeatedly with tris EDTA buffer of pH 7.2.

The concentrated antigen so obtained is then inactivated by usual methods and further purified using an anion exchange matrix to obtain purified rabies antigen. The antigen is then diafiltered and blended as vaccine The HIMAX purification yields with rabies antigen in all the intermediate steps are given in table IV.

Flow chart for HIMAX in Rabies Vaccine production

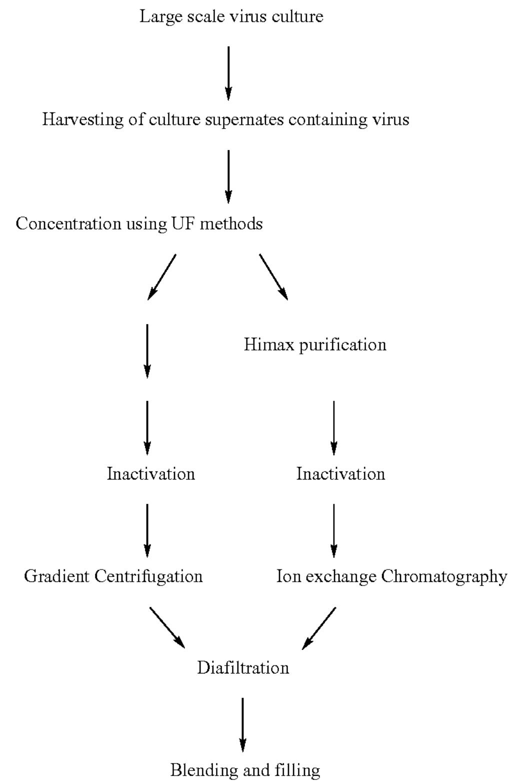

TABLE IV

| Rabies antigen purification by HIMAX | | | |
|---|---|---|---|
| Sample lot no | Volume | HA activity per ml | Percent recovery |
| RAB Bulk 1-2003 | 1000 ml | 1280 | — |
| After HIMAX | 120 ml | 10240 | 96 |
| RAB Bulk 2-2003 | 800 ml | 2560 | — |
| After HIMAX | 95 ml | 20480 | 95 |
| RAB Bulk 3-2003 | 3000 ml | 1280 | — |
| After HIMAX | 180 ml | 20480 | 96 |

Example III

Hepatitis A Antigen Production from a Cell Culture Pathway

The large scale virus culture facilitates obtaining Hepatitis A virus in the culture as cell bound virus. Traditionally the harvests of virus are obtained as cell lysates which are clarified, inactivated and then purified using the gradient ultracentrifugation on sucrose in a continuous or batch mode zonal centrifuge. In the present invention the culture lysates are initially purified by the use of HIMAX for primary capturing of Hepatitis A antigen by a batch procedure in which salts of divalent cations such as Calcium Magnesium and Zinc are added to yield a final concentration of 8 to 10 fold (W/V)

resulting in the formation of white insoluble matrix further interacts. The insitu formation of the matrix further interact with the antigen and this process of protein capturing is referred as HIMAX technology. This matrix was separated by centrifugation between 7000 g to 10,000 g and the bound antigen was desorbed repeatedly with tris EDTA buffer of pH 7.2.

The concentrated antigen so obtained is then inactivated by usual methods and further purified using an anion exchange matrix to obtain purified Hepatitis A antigen. The antigen is then diafiltered and blended as vaccine The HIMAX purification yields with Hepatitis A antigen in all the intermediate steps are given in table V.

Flow chart for HIMAX in Hepatitis A production

Large scale virus culture
↓
Harvesting of culture Lysates containing virus
↓
Clarification by centrifugation
↙         ↘
         Himax purification
              ↓
Inactivation          Inactivation
    ↓                      ↓
Gradient Centrifugation    Ion exchange Chromatography
         ↘         ↙
         Diafiltration
              ↓
         Blending and filling

TABLE V

-Hepatitis A antigen purification by HIMAX

| Sample Lot No | Volume | ELISA units per ml | Recovery percent |
|---|---|---|---|
| HAV Lot 2-03 | 100 ml | 2560 | |
| After HIMAX | 9 ml | 20480 | 72 |
| HAV lot 3-03 | 150 ml | 1280 | |
| After HIMAX | 16 ml | 10120 | 84.3 |
| HAV lot 4-03 | 90 ml | 2560 | |
| After HIMAX | 90 ml | 20480 | 88 |

Example IV

Diptheria Toxoid is a Purified Protein Derived from *Corynebacterium diphtheriae* Culture The Cell harvest is subjected to centrifugation or filtration and the toxin in the supernatant is converted to toxoid by the addition of 0.60% of formalin. The toxin is incubated at 33 C for 6 weeks for the conversion to toxoid.

The detoxification is confirmed by animal experimentation. In the traditional process the toxoid is concentrated, fractionated with Ammonium sulphate, dialysed and sterile filtered. The activity is measured by flocculation test. The recovery of toxoid is tabulated in table VI.

In the purification by the HIMAX technology, the Toxoid is subjected to capturing, by the batch mode, in which salts of divalent cations such as Zn, Ca, Mg are added at 0.2% to 10% (w/v) in the presence of phosphates, chlorides or acetates to form white insoluble matrix. The matrix is separated from the solution by Centrifugation between 7000 g to 10,000 g and the bound antigen is solubilized in Phosphate buffer containing 10-200 mM EDTA pH 6.8 to 7.2. The purified samples are checked by SDS-PAGE Electrophoresis.

The solution is Ultrafiltrated and the bulk is sterile filtered with 0.22 micron. The results are tabulated in Table VII.

Flow Chart for Diphtheria toxoid production using HIMAX technology

Cell Harvest
↓
Centrifugation/Filtration
↓
Toxin
↓
Toxoid
↓
Toxoid Concentration
↓
Ammonium Sulphate Fractionation
↓
Ultrafiltration
↓
Sterile Filtration

TABLE VI (Traditional method of purification of Ditheria toxoid)

| S. No | Purification Step | Activity (%) |
|---|---|---|
| 1. | Cell supernatant | 100 |
| 2 | Toxoid | 90 |
| 3 | Concentrated Toxoid | 90 |
| 4 | Ammonium Sulphate Fraction | 70 |
| 5 | Ultrafiltration | 70 |
| 6. | Sterile filtration | 70 |

TABLE VII (Purification of Diphtheria by HIMAX technology)

| S. No | Purification Step | Activity (%) |
|---|---|---|
| 1. | Cell supernatent | 100 |
| 2 | Toxoid | 90 |
| 3 | HIMAX purified bulk | 85 |
| 4 | Ultrafiltration | 85 |
| 5 | Sterile filtration | 85 |

Example V

Tetanus Toxoid is a Purified Protein Derived from *Clostridium tetani* Cultures The Cell harvest is subjected to centrifugation or filtration and the toxin in the supernatant is converted to toxoid by the addition of 0.40% of formalin. The toxin is incubated at 35 C to 36 C for 4 weeks during which the toxin is converted to toxoid.

The detoxification is confirmed by animal experimentation. In the conventional process the toxoid is concentrated, fractionated with Ammonium sulphate, dialysed and sterile filtered. The activity is measured by flocculation test. The recovery of toxoid is tabulated in VIII In the purification by the HIMAX technology, the Toxoid is subjected to capturing by the batch procedure in which salts of divalent cations such as Zn, Ca, Mg are added at 0.2% to 10% (w/v) in the presence of phosphates, chlorides or acetates to form white insoluble matrix. The matrix is separated from the solution by Centrifugation between 7000 g to 10,000 g and the bound antigen is solubilized in Phosphate buffer containing 10-200 mM EDTA Ph 6.8 to 7.2

The purity is checked by SDS-Electrophoresis.

The solution is Ultrafiltrated and the bulk is sterile filtered with 0.22 micron. The results are tabulated in Table IX

TABLE VIII (Purification of Tetanus toxoid by conventional process)

| S. No | Purification Step | Activity (%) |
|---|---|---|
| 1. | Cell supernatent | 100 |
| 2 | Toxoid | 90 |

TABLE VIII-continued (Purification of Tetanus toxoid by conventional process)

| S. No | Purification Step | Activity (%) |
|---|---|---|
| 3 | Concentrated Toxoid | 90 |
| 4 | Ammonium Sulphate Fraction | 70 |
| 5 | Ultafilration | 70 |
| 6. | Sterile filtration | 70 |

TABLE IX (Purification of Tetanus toxoid by HIMAX technology)

| S. No | Purification Step | Activity (%) |
|---|---|---|
| 1. | Cell supernatent | 100 |
| 2 | Toxoid | 90 |
| 3 | HIMAX purified bulk | 87 |
| 4 | Ultrafiltration | 85 |
| 5 | Sterile filtration | 85 |

We claim:

1. A process of purification of a protein of interest from an insoluble fraction, the process consisting of the steps:
    (a) forming an insoluble matrix by the addition of divalent ionic salt having a concentration ranging from 0.2% to 10% with counter ions of either phosphate, chloride and/or acetate solution to the insoluble fraction;
    (b) subjecting the insoluble matrix obtained in step (a) to centrifugation to form a pellet;
    (c) repeatedly subjecting the pellet from step (b) to a desorption process to release said protein(s) from said insoluble pellet by using either TRIS buffer of pH 8.0 to 8.5 or TRIS with EDTA buffer at pH 7.0 to 8.0 to obtain a desorbate;
    (d) recovering said protein from the desorbate through ultrafiltration, chromatography on colloidal silica, hydrophobic chromatography, affinity chromatography, ion exchange, diafiltration, sterile filtration or a combination thereof.

2. The process of claim 1, wherein said protein is selected from the group consisting of rabies antigen, hepatitis A antigen, hepatitis B antigen, diphtheria toxoid and tetanus toxoid.

* * * * *